United States Patent [19]
Shimizu et al.

[11] Patent Number: 5,808,166
[45] Date of Patent: Sep. 15, 1998

[54] METHOD FOR PRODUCING 3,4-DIHYDROXY-3-CYCLOBUTENE-1,2-DIONE

[75] Inventors: Ikuo Shimizu; Takeshi Usami; Hiroshi Toyoda; Asako Okajima; Shoshiro Matsushita, all of Yokkaichi, Japan

[73] Assignee: Kyowa Yuka Co., Ltd., Tokyo, Japan

[21] Appl. No.: 973,157

[22] PCT Filed: Apr. 2, 1997

[86] PCT No.: PCT/JP97/01133

§ 371 Date: Dec. 3, 1997

§ 102(e) Date: Dec. 3, 1997

[87] PCT Pub. No.: WO97/37961

PCT Pub. Date: Oct. 16, 1997

[30] Foreign Application Priority Data

Apr. 9, 1996 [JP] Japan ................................. 8-086410

[51] Int. Cl.$^6$ ................................................. C07C 45/43
[52] U.S. Cl. .................................... 568/348; 568/338
[58] Field of Search ............................. 568/348, 338

[56] References Cited

U.S. PATENT DOCUMENTS

| | | | |
|---|---|---|---|
| 4,997,745 | 3/1991 | Kawamura et al. | 430/281 |
| 5,391,741 | 2/1995 | Shimizu et al. | 544/345 |

FOREIGN PATENT DOCUMENTS

| | | |
|---|---|---|
| 0379200 | 7/1990 | European Pat. Off. . |
| 0442431 | 8/1991 | European Pat. Off. . |
| 2-48665 | 2/1990 | Japan . |
| 2-306247 | 12/1990 | Japan . |
| 4-106400 | 4/1992 | Japan . |
| 4-330034 | 11/1992 | Japan . |
| 5-5005 | 1/1993 | Japan . |
| 5-96173 | 4/1993 | Japan . |

OTHER PUBLICATIONS

Bellus et al, Helvetica Chimica Acta, vol. 61, No. 173 (1978) 1784–1813.
Bellus et al, J. Org. Chem., vol. 44, No. 8 (1979) 1208–1211.
Pericas et al, Tetrahedron Letters, No. 50 (1977) 4437–38.
Silvestri et al, Electrochimica Acta., vol. 23 (1978) 413–417.
Law et al, Chem. Rev., vol. 93 (1993) 449–486.

*Primary Examiner*—Gary Geist
*Assistant Examiner*—Sreeni Padmanabhan
*Attorney, Agent, or Firm*—Fitzpatrick, Cella, Harper & Scinto

[57] ABSTRACT

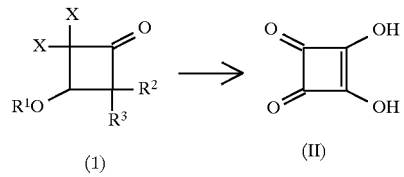

In the formulae, $R^1$ represents alkyl; and $R^2$, $R^3$ and X independently represent halogen. The present invention relates to a method for producing 3,4-dihydroxy-3-cyclobutene-1, 2-dione of general formula (II) by hydrolyzing 3-alkoxy-2, 2, 4, 4-tetrahalogenocyclobutanone derivative of general formula (I).

4 Claims, No Drawings

METHOD FOR PRODUCING 3,4-DIHYDROXY-3-CYCLOBUTENE-1,2-DIONE

This is the U.S. National Stage Application of PCT/JP97/01133 filed Apr. 2, 1997 now WO 97/37961 published Oct. 16, 1997.

TECHNICAL FIELD

The present invention relates to a method for producing 3,4-dihydroxy-3-cyclobutene-1,2-dione.

3,4-Dihydroxy-3-cyclobutene-1,2-dione (usual name: squaric acid) is useful as a raw material for functional materials of medicines, electrophotographic photoreceptors, recording materials for rewritable optical discs, photosensitizers, etc. (Chem. Rev., 93, 449 (1993); Japanese Published Unexamined Patent Application Nos. 5-306285, 2-306247, 2-48665, 5-5005, and 5-96173).

BACKGROUND ART

Various methods for producing 3,4-dihydroxy-3-cyclobutene-1,2-dione have heretofore been known. However, the known methods are problematic in that the process for those is complicated and takes much time, that the starting materials for those are difficult to synthesize, that they require strict conditions, that their yield is low, and that they require special equipment. For example, the known methods include (1) a method of using triketene as the starting material (B. Jackson et al., EP 442431); (2) a method of using 3-hydroxy-3-cyclobutene-1,2-dione as the starting material (D. Bellus et al., Helv. Chim. Acta, 61, 1784 (1978)); (3) a method of using tetraalkoxyethylene as the starting material (D. Bellus, J. Org. Chem., 44, 1208 (1979)); (4) a method of using dialkoxyacetylene as the starting material (M. A. Pericas, Tetrahedron Letter, 4437 (1977)); (5) a method of using tetrahalogenoethylene as the starting material (J. Amer. Chem. Soc., 81, 3480 (1959)); (6) a method of using hexachlorobutadiene as the starting material (P. Hagenberg et al., Ger. Offen. 1568291); and (7) a method of using carbon monoxide as the starting material (G. Silvestri et al., Electrochim. Acta, 23, 413 (1978)). However, those methods are all problematic in that, in (1), it is difficult to ensure a large quantity of the starting material, triketene, which is a side product in the production of diketene; in (2), the starting material is obtained in biological solid cultivation with poor productivity or in chemical synthesis that requires a complicated and long process; in (3), the starting material is difficult to produce, and its yield is low; in (4), the starting material is difficult to produce; in (5), the starting material is difficult to produce, and its production requires a complicated and long process; in (6), the yield of the product is low; and in (7), the production requires special equipment.

DISCLOSURE OF THE INVENTION

The present invention relates to a method for producing 3,4-dihydroxy-3-cyclobutene-1,2-dione of general formula (II):

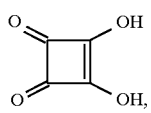

which comprises hydrolyzing a 3-alkoxy-2,2,4,4-tetrahalogenocyclobutanone derivative of general formula (I):

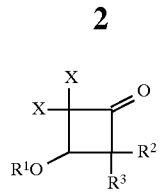

wherein $R^1$ represents alkyl, and $R^2$, $R^3$ and X independently represent halogen.

The present invention also relates to a method for producing 3-alkoxy-2,2,4,4-tetrahalogenocyclobutanone derivatives of formula (I):

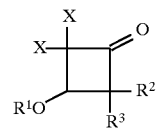

wherein $R^1$, $R^2$, $R^3$ and X have the same meanings as above, which comprises halogenating a 3-alkoxy-2,2-dihalogenocyclobutanone derivative of general formula (III):

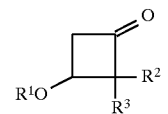

wherein $R^1$, $R^2$ and $R^3$ have the same meanings as above, with a halogenating agent.

The present invention further provides 3-alkoxy-2,2,4,4-tetrahalogenocyclobutanone derivatives of formula (I):

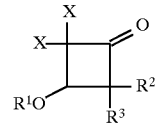

wherein $R^1$, $R^2$, $R^3$ and X have the same meanings as above.

Compounds of formulae (I), (II) and (III) are hereinafter referred to as compound (I), compound (II) and compound (III), respectively.

In the definitions of the groups in formulae (I) and (II), the alkyl means a straight-chain or branched alkyl group having 1 to 18 carbon atoms, including methyl, ethyl, propyl, isopropyl, butyl, isobutyl, sec-butyl, tert-butyl, pentyl, isoamyl, neopentyl, 2-pentyl, 3-pentyl, hexyl, heptyl, octyl, 2-ethylhexyl, nonyl, decyl, dodecyl, pentadecyl and octadecyl; and the halogen means fluorine, chlorine, bromine and iodine.

The invention is described in detail hereinunder.

Compounds (II) can be produced according to the following process:

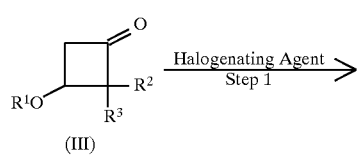

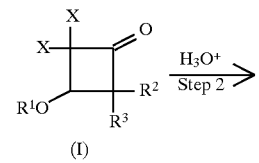

-continued

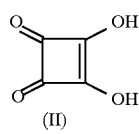

wherein $R^1$, $R^2$, $R^3$ and X have the same meanings as above.

Step 1

The starting compound (III) (3-alkoxy-2,2-dihalogenocyclobutanone derivative) can be easily obtained in known methods (J. Org. Chem., 32, 3703 (1967); Helv. Chim. Acta, 61, 1784 (1978)), or based on the known methods, for example, by reacting an alkyl vinyl ether with a dihalogenoacetyl chloride in the presence of triethylamine, followed by hydrolyzing the resulting intermediate.

Compound (I) (3-alkoxy-2,2,4,4-tetrahalogenocyclobutanone derivative) can be obtained by halogenating compound (III) with 2 to 5 equivalents, preferably 2 to 3 equivalents of a halogenating agent optionally in the presence of 2 to 5 equivalents, preferably 2 to 3 equivalents of a basic compound, or a catalytic amount to 3 equivalents of a phosphorus compound, or their mixture, in a solvent inert to the reaction. The halogenating agent includes chlorine, bromine, iodine, phosphorus pentachloride, sulfuryl chloride, N-bromosuccinimide, and N-chlorosuccinimide. The basic compound includes organic basic compounds such as pyridine, triethylamine and quinoline; inorganic basic compounds such as sodium hydroxide, potassium hydroxide, sodium carbonate, potassium carbonate and sodium hydrogencarbonate; basic organic acid salts such as sodium acetate and potassium acetate; and their mixtures. The phosphorus compound includes phosphorus tribromide and phosphorus trichloride. The solvent inert to the reaction includes ethers such as diethyl ether, diisopropyl ether, tetrahydrofuran, 1,4-dioxane and tert-butyl methyl ether; halogenated hydrocarbons such as chloroform, dichloromethane and 1,2-dichloroethane; alcohols such as methanol, ethanol, propanol and isopropanol; aromatic hydrocarbons such as benzene, toluene and xylene; N,N-dimethylformamide, dimethylsulfoxide, water; and mixed solvents comprising any of those. The reaction is effected at a temperature between room temperature and 100° C., and is finished within 10 minutes to 3 hours.

Step 2

Compound (II) (3,4-dihydroxy-3-cyclobutene-1,2-dione) can be obtained by heating compound (I) with an acidic aqueous solution in the presence or absence of a solvent. The solvent includes ethers such as diethyl ether, diisopropyl ether, tetrahydrofuran, 1,4-dioxane and tert-butyl methyl ether; halogenated hydrocarbons such as chloroform, dichloromethane and 1,2-dichloroethane; alcohols such as methanol, ethanol, propanol and isopropanol; aromatic hydrocarbons such as benzene, toluene and xylene; N,N-dimethylformamide, dimethylsulfoxide, acetic acid; and mixed solvents comprising any of those. The acidic aqueous solution includes aqueous sulfuric acid, aqueous hydrochloric acid, aqueous acetic acid, aqueous nitric acid, aqueous phosphoric acid, aqueous trifluoroacetic acid, and their mixtures. The concentration of the acidic aqueous solution may be 1 to 90% by weight, preferably to 60% by weight. The reaction is effected at a temperature between 80° and 120° C., preferably between 90° and 110° C., and is finished in 1 to 48 hours.

The intermediate and the final product produced in the above-mentioned process can be isolated and purified through ordinary purification generally employed in organic synthetic chemistry, for example, distillation, filtration, extraction, washing, drying, concentration, recrystallization and/or chromatography. The intermediate may be subjected to the next reaction without being specifically isolated or purified.

Compound (I) and compound (II) may exist in the form of adducts with water or solvents, which are also within the scope of the present invention.

Examples of the invention are described below, which, however, are not intended to restrict the scope of the invention.

BEST MODES OF CARRYING OUT THE INVENTION

Example 1

Production of 2,2-dibromo-4,4-dichloro-3-isobutoxycyclobutanone

With cooling with ice, bromine (507.4 g) and pyridine (250.6 g) were added to a solution as prepared by dissolving 2,2-dichloro-3-isobutoxycyclobutanone (262.4 g) in tert-butyl methyl ether(1 liter), and then reacted at 44° C. for 1 hour. The reaction mixture was washed with 400 g of an aqueous solution of 10 wt. % sodium thiosulfate to thereby remove the aqueous layer. The solvent was evaporated under reduced pressure, and the residue was subjected to distillation to obtain 2,2-dibromo-4,4-dichloro-3-isobutoxycyclobutanone(360 g). The reaction yield was 96.9% (gas chromatography). The yield of the isolated product was 79%.

| Elementary Analysis: | H | C |
|---|---|---|
| Calculated (%): | 2.73 | 26.05 |
| Found (%): | 2.78 | 26.05 |
| Boiling Point: | 98 to 99° C./0.7 to 0.8 mmHg | |

Example 2

Production of 3,4-dihydroxy-3-cyclobutene-1,2-dione

A mixture of 2,2-dibromo-4,4-dichloro-3-isobutoxycyclobutanone (2 g) obtained in Example 1, an aqueous solution(3 g) of 33 wt. % sulfuric acid and propanol(4 ml) was refluxed for 22 hours.

Most propanol was evaporated, the resulting residue was cooled to room temperature, and the precipitate formed was taken out through filtration to obtain 3,4-dihydroxy-3-cyclobutene-1,2-dione (0.47 g). The yield was 76%.
$^1$H—NMR (DMSO-$d_6$): δ13.7 ppm
$^{13}$C—NMR (DMSO-$d_6$): δ189.9 ppm Example 3

Production of 2,2-dibromo-4,4-dichloro-3-ethoxycyclobutanone 2,2-Dibromo-3-ethoxycyclobutanone(10 g) and 27.1 g of an aqueous solution of 20% sodium acetate were added to tert-butyl methyl ether (83 ml), to which were added bromine(21.1 g) and pyridine(5.22 g) at 10° C., and then reacted at 44° C. for 1 hour. The aqueous layer was removed, and the organic layer was washed with 16 ml of an aqueous solution of 10 wt. % sodium thiosulfate and saturated saline(8 ml), whereby the remaining aqueous layer was further removed. The solvent was evaporated under reduced pressure, and the residue was subjected to distillation to obtain 2,2-dibromo-4,4-dichloro-3-ethoxycyclobutanone. The reaction yield was 98.3% (gas chromatography). The yield of the isolated product was 68.6%.

| Elementary Analysis: | H | C |
|---|---|---|
| Calculated (%): | 1.77 | 21.14 |
| Found (%): | 1.79 | 20.97 |
| Boiling Point: | | 79° C./0.5 mmHg |

Example 4

Production of 2,2-dibromo-4,4-dichloro-3-propoxycyclobutanone

Substantially the same procedure as in Example 3 was repeated using 2,2-dichloro-3-propoxycyclobutanone(10.83 g) in place of 2,2-dichloro-3-ethoxycyclobutanone(10 g) to obtain 2,2-dibromo-4,4-dichloro-3-propoxycyclobutanone. The reaction yield was 90.9% (gas chromatography). The yield of the isolated product was 67.8%.

| Elementary Analysis: | H | C |
|---|---|---|
| Calculated (%): | 2.27 | 23.69 |
| Found (%): | 2.36 | 23.84 |
| Boiling Point: | | 101° C./1.2 mmHg |

Example 5

Production of 2,2-dibromo-4,4-dichloro-3-octadecyloxycyclobutanone 2,2-Dichloro-3-octadecyloxycyclobutanone(22.3 g) and 27.1 g of an aqueous solution of 20% sodium acetate were added to tert-butyl methyl ether (83 ml), to which were added bromine (21.1 g) and pyridine(5.22 g) at 10° C., and then reacted at 40° to 50° C. for 1 hour. After the reaction, the reaction mixture was cooled to room temperature, and then washed with saturated saline(15 ml) and 24 ml of an aqueous solution of 10 wt. % sodium thiosulfate to thereby remove the aqueous layer. The solvent was evaporated under reduced pressure to obtain 2,2-dibromo-4,4-dichloro-3-octadecyloxycyclobutanone(28.3 g). The yield was 91.2%.
$^1$H—NMR (CDCl$_3$): δ (ppm) 0.88 (3 H, t, J=7 Hz), 1.3–1.48 (30 H, m), 1.77 (2 H, sextet, J=7Hz), 3.83–3.93 (2 H, m), 4.66 (1 H, s)
$^{13}$C—NMR (CDCl$_3$): δ (ppm) 14.1, 22.7, 25.9, 29.3–29.7, 31.9, 57.0, 73.1, 82.9, 90.1, 184.4

Example 6

Production of 3,4-dihydroxy-3-cyclobutene-1,2-dione

A mixture of 2, 2-dibromo-4, 4-dichloro-3-ethoxycyclobutanone (20 g) obtained in Example 3, 32.5 g of an aqueous solution of 33 wt. % sulfuric acid and isopropanol(43.3 ml) was refluxed for 6 hours. The volatile component was evaporated by heating at ordinary pressure, then the residue was cooled to 10° C., and the precipitate formed was taken out through filtration to obtain 3,4-dihydroxy-3-cyclobutene-1,2-dione (5.18 g). The yield was 76.7%.

Example 7

Production of 3,4-dihydroxy-3-cyclobutene-1,2-dione

A mixture of 2, 2-dibromo-4, 4-dichloro-3-propoxycyclobutanone (20 g) obtained in Example 4, 31.2 g of an aqueous solution of 33 wt. % sulfuric acid and isopropanol(41.6 ml) was refluxed for 6 hours. The volatile component was evaporated by heating at ordinary pressure, then the residue was cooled to 10° C., and the precipitate formed was taken out through filtration to obtain 3,4-dihydroxy-3-cyclobutene-1,2-dione (4.93 g). The yield was 76.1%.

Example 8

Production of 3, 4-dihydroxy-3-cyclobutene-1,2-dione 2,2-Dichloro-3-octadecyloxycyclobutanone (137.5 g) and 156.9 g of an aqueous solution of 20% sodium acetate were added to 200 ml of tert-butyl methyl ether, to which were added bromine(122.3 g) and pyridine(30.26 g) at 10° to 20° C., and then reacted at 44° C. for 1 hour. The aqueous layer was removed, and the organic layer was washed with 90 ml of an aqueous solution of 10 wt. % sodium thiosulfate and saturated saline (45 ml), whereby the remaining aqueous layer was further removed. Tert-butyl methyl ether was evaporated under reduced pressure, and 157.8 g of an aqueous solution of 33 wt. % sulfuric acid and isopropanol (600 ml) were added to the residue, and refluxed for 6 hours. The volatile component was removed by heating at ordinary pressure, chloroform(800 ml) was added to the residue, and the precipitate thus formed was taken out through filtration to obtain 3,4-dihydroxy-3-cyclobutene-1,2-dione (22.05 g). The yield was 57.3%.

INDUSTRIAL APPLICABILITY

The present invention provides a method for producing 3,4-dihydroxy-3-cyclobutene-1,2-dione, which is advantageous in that easily available raw materials are reacted under mild conditions in any ordinary equipment for chemical synthesis, that the yield of the product is high, and that the method itself is simple as comprising a few steps.

We claim:
1. A method for producing 3,4-dihydroxy-3-cyclobutene-1,2-dione of general formula (II):

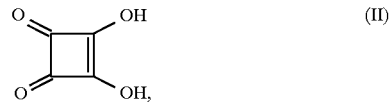

which comprises hydrolyzing a 3-alkoxy-2,2,4,4-tetrahalogenocyclobutanone derivative of general formula (I):

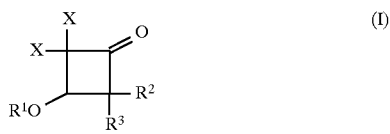

wherein $R^1$ represents alkyl, and $R^2$, $R^3$ and X independently represent halogen.

2. A method for producing 3-alkoxy-2,2,4,4-tetrahalogenocyclobutanone derivatives of formula (I):

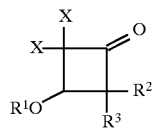
(I)

which comprises halogenating a 3-alkoxy-2,2-dihalogenocyclobutanone derivative of general formula (III):

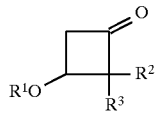
(III)

wherein $R^1$, represents alkyl, and $R^2$, $R^3$ and X independently represent halogen, with a halogenating agent.

3. A method for producing 3,4-dihydroxy-3-cyclobutene-1,2- dione of general formula (II):

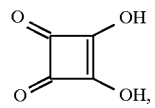
(II)

which comprises halogenating a 3-alkoxy-2,2-dihalogenocyclobutanone derivative of general formula (III):

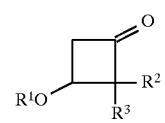
(III)

with a halogenating agent, to give a 3-alkoxy-2,2,4,4-tetrahalogenocyclobutanone derivative of general formula (I):

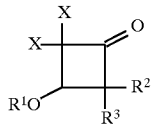
(I)

wherein $R^1$ represents alkyl, and $R^2$, and $R^3$ and X independently represent halogen, followed by hydrolyzing the resulting derivative without isolating it.

4. 3-Alkoxy-2,2, 4, 4-tetrahalogenocyclobutanone derivatives of formula (I):

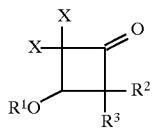
(I)

wherein $R^1$ represents alkyl, and $R^2$, $R^3$ and X independently represent halogen.

* * * * *